(12) United States Patent
Guzelsu et al.

(10) Patent No.: US 6,324,419 B1
(45) Date of Patent: Nov. 27, 2001

(54) APPARATUS AND METHOD FOR NON-INVASIVE MEASUREMENT OF STRETCH

(76) Inventors: Nejat Guzelsu, 244 Edgerstoune Rd., Princeton, NJ (US) 08540; Thomas W. Findley, 36 Warfield Ave., Upper Montclair, NJ (US) 07043; John Federici, 847 Shackamaxon Dr., Westfield, NJ (US) 07090; Hans R. Chaudhry, 176 Prestick Way, Edison, NJ (US) 08820; Arthur B. Ritter, 46 Fowler Dr., West Orange, NJ (US) 07052

( * ) Notice: Subject to any disclaimer, the term of this patent is extended or adjusted under 35 U.S.C. 154(b) by 0 days.

(21) Appl. No.: 09/179,571

(22) Filed: Oct. 27, 1998

(51) Int. Cl.[7] ....................................................... A61B 5/00
(52) U.S. Cl. ............................................ 600/476; 600/473
(58) Field of Search ................................... 600/476, 473, 600/475; 356/369, 32, 33, 34, 35

(56) References Cited

U.S. PATENT DOCUMENTS

| | | |
|---|---|---|
| 3,273,381 | 9/1966 | Webb . |
| 3,950,987 | 4/1976 | Slezinger et al. . |
| 4,010,632 | 3/1977 | Slezinger et al. . |
| 4,177,798 * | 12/1979 | Leveque et al. ................ 128/774 |
| 4,321,831 | 3/1982 | Tomlinson et al. . |
| 4,377,343 | 3/1983 | Monson . |
| 4,515,473 | 5/1985 | Mermelstein . |
| 4,668,085 * | 5/1987 | Pitt et al. ........................... 356/32 |
| 4,693,606 | 9/1987 | Podolsky et al. . |
| 4,703,918 | 11/1987 | Pindera . |
| 4,958,929 | 9/1990 | Kondo . |
| 5,028,130 | 7/1991 | Hoffmann et al. . |
| 5,054,502 * | 10/1991 | Courage .......................... 128/744 |
| 5,064,270 | 11/1991 | Turpin et al. . |
| 5,170,666 | 12/1992 | Larsen . |
| 5,278,776 * | 1/1994 | Fisher et al. .................... 364/508 |
| 5,398,681 | 3/1995 | Kupershmidt . |
| 5,400,131 * | 3/1995 | Stockley et al. .................. 356/33 |
| 5,677,635 | 10/1997 | Fujii et al. . |
| 5,909,273 * | 6/1999 | Malvern ......................... 356/35.5 |
| 5,944,667 * | 8/1999 | Leveque et al. ................. 600/473 |
| 6,032,071 * | 2/2000 | Binder ............................. 600/476 |

OTHER PUBLICATIONS

Anderson et al., 1990a, Photodermatol. Photoimmunol. Photomed. 7:5–12.
Anderson et al., 1990b, Photodermatol. Photoimmunol. Photomed. 7:249–57.
Anderson et al, 1981, J. Investigative Dermatol. 77:13–19.
Anderson et al., 1982, Optical Properties of Human Skin. In "The Structure of Photomedicine" Ed. By J.D. Regan et al., Plenum Press New York pp. 147–194.
Argenta et al., 1990, Principles and Techniques of Tissue Expansion. In "Plastic Surgery vol. 1: General Principles" Ed. By J.G. McCarthy, W.B. Saunders Com. pp. 475–507.
Bjerring et al., 1987, Photodermatol. Photoimmunol. Photomed. 4:167–171.
Bolton et al., 1988, Wound Healing and Integumentary System. In "Experimental Surgery and Physiology". Ed. By M. Swindle et al., Williams and Wilkinson Baltimore pp. 1–9.
Bucalo et al., 1995, Dermatol. Surg. 21:210–212.
Cacou et al., 1995, J. R. Coll. Surg. Edinb. 40:38–41.

(List continued on next page.)

Primary Examiner—Marvin M. Lateef
Assistant Examiner—Eleni Mantis Mercader
(74) Attorney, Agent, or Firm—Klauber & Jackson

(57) ABSTRACT

A method and apparatus for noninvasive, non-contacting measurement of stretches and deformations on the surface of a material or an object by utilizing changes which occur in the reflection characteristics of the material due to an applied stretch load is presented. The present invention may assume various embodiments for different applications, such as soft tissue stretch determination, plastic material deformation measurements and sensors which can be integrated into various measurement devices.

66 Claims, 6 Drawing Sheets

OTHER PUBLICATIONS

Chaudhry et al., 1997, Mathematical Modeling of Wound Closure Stresses. J. Biomechanics Under Revision.

Cheong et al., 1990, IEEE J. Quantum Electro. 26:2166–2185.

Cohen et al., 1976, J. Biomechanics. 9:175–184.

Dawson et al., 1980, Phys. Med. Biol. 25:695–709.

Gibson, 1990, Physical Properties of Skin. In "Plastic Surgery vol. 1: General Principles" Ed. By J. G. McCarthy, W.B. Saunders Com. pp. 207–220.

Jacques, 1991, The Role of Skin Optics Diagnostic and Therapeutic Uses of Laser. In "Lasers in Dermatology" Ed. By R. Steiner et al., Springer–Verlag Berlin p. 1–21.

Laemmli, 1970, Nature, 227:680–685.

Lanir, 1979, Biorheology 16:191–202.

Lanir et al., 1974a, J. Biomechanics, 7:29–34.

Lanir et al., 1974b, J. Biomechanics, 7:171–182.

Larrabee et al., 1984, Ann. Otol. Rhinol. Laryngol. 93:112–115.

Lokberg, 1991, Speckles and speckle techniques for bio--medical applications. In "Bioptics: Optics in Biomedicine and Environmental Sciences", Ed. By A.M. Scheggi et al., SPIE 1524:35–47.

Marchesini et al., 1992, J. Photochem. Photobiol. B: Biol. 16:127–140.

Marks et al., 1986, J. Trauma 26:913–917.

Marks et al. 1985, J. Trauma, 25:947–951.

Nollert et al., 1989, Biochimica et Biophysica Acta. 1005:72–78.

Paul et al., 1997, Int. J. Biochem. Cell Biol. 29:211–220.

Pereira et al., 1991, J. Biomechanics. 24:157–162.

Reihsner et al., 1995, Med. Eng. Phys. 17:304–313.

Sinichkin et al., 1996, Physical Optics. 80:228–234.

Sumpio et al., 1990, Surgery 108:277–282.

Sumpio et al. 1987, j. Vasc. Surg. 6:252–256.

Tong et al., 1976, J. Biomechanics. 9:649–657.

Tuchin, 1993, Laser Physics. 3:767–820.

Van Gemert et al., 1989, Biomed. Engng. 36:1146–1154.

Wilson et al., 1990. Optical Reflectance and Transmittance of Tissues: principles and Applications 26:2186–2199.

Zeng et al., 1993, Phys. Med. Biol. 38:231–240.

* cited by examiner

APPARATUS AND METHOD FOR NON-INVASIVE MEASUREMENT OF STRETCH

FIELD OF THE INVENTION

The present invention relates to the measurement of stretch, deformation and stress generally and, more particularly, but not by way of limitation, to a novel apparatus and method for non-invasively obtaining measurements of stretch.

BACKGROUND OF THE INVENTION

Techniques of light reflection have been used to study the intrinsic properties of skin, (such as the adsorption and the scattering) coefficients, and mathematical models have been developed to take into account these properties. These studies were performed mainly to determine skin chromophores due to changes in the skin structure and the effects of pigments and hemoglobin on the reflection characteristics of the skin. Specific areas include skin erythema due to ultraviolet light exposure, and mechanical compression of the skin. Another technique, laser speckle and holography has been used to measure small displacements of skin. However, this interferometric technique has some severe technical difficulties for in vivo use due to motion of the subject. Also a laser diffraction apparatus has been designed to measure the sarcomere length of the muscles in-vivo, which is useful for tendon transfer procedures. The diffraction patterns of the striated muscle fibril due to Z dark lines have been utilized in this technique. This method will not work for skin or other soft tissues due to the lack of fine natural grating lines for laser diffraction.

The optical properties of skin are related to its structure and its chemical composition such that when a beam of light reaches the skin surface, part of it will be reflected by the surface directly, while the rest will be refracted and transmitted into the skin. The direct reflection of light by a generally smooth surface, where the angle of reflected light is equal to angle of incident light is called specular reflection and is related only to the refractive index change between the air and reflecting medium. By nature, most of the reflection of light from skin is diffuse rather than specular. The intensity and angular distribution of diffusion reflection is determined by transmission and scattering properties of the skin tissue. After diffuse reflection from the top layer of the skin, a portion of the light transmitted through the top layer and into the skin will be scattered and absorbed by the skin tissue. After multiple scattering and reflection from the different layers of skin, some of the transmitted light will re-emerge through the air-stratum interface into the air as part of the total reflected light intensity.

Soft tissue stretch is commonly measured by marking the tissue on its surface using a pen or colored tape and recording the changes in marker position with stretch. The recording device can be photographic film or video. In this method a large distance between the marked lines on the skin is needed to reduce the experimental error in finding out the stretch. Commercially available video extensometers of this type are manufactured by Instron Corp. Canton Mass. Such devices are rather big and can best measure flat, well-marked specimens. For in-vivo measurements, however, the curvature of the skin due to natural body contour interferes with the exact measurements of the distances between the marked points.

Mechanical properties of skin, such as elastic and viscoelastic, have been investigated experimentally and theoretical models have been proposed.

Wounds created by accidents or surgical procedures involve trauma to both the skin and the underlying tissue. Wound healing proceeds through several stages, including an initial inflammatory response and cell proliferation and migration. The inflammatory response at the wound site involves leukocyte infiltration and the local release of chemical mediators of inflammatory such as histamine, platelet activating factor, leukotrienes and endothelin-1 by leukocytes and endothelial cells. It has been well established that cellular production and release of inflammatory mediators are altered by mechanical stress. Physical properties of skin play a dominant role in closure of wounds. When the skin is stretched during suturing, stresses are produced. Skin tension is of particular importance in wound healing. High tension across a sutured wound is likely to produce a stretched hypertropic scar at that site. Better scars are produced when the axis of a wound are placed parallel to Langer's lines compared to the case when the axis cross the lines. Langer's lines described as the natural tension lines exist in the skin. A circular incision on the skin becomes an elliptical shape where the long axis of the ellipse lies parallel to the Langer's lines. Dehiscence, ischemia or necrosis may be expected in regions of high stresses through compromise of circulation in the subdermal vascular plexus. Blood flow is inversely proportional to wound closure tension as observed in animal studies. Therefore, it is worthwhile to determine stresses and/or deformations accurately for a given pattern of suturing of the wound. A preferred suturing pattern and wound geometry should produce low average tensile stresses with the lowest possible stress gradient at the critical points of the wound edges.

The principles and the techniques of tissue expansion procedure have been widely used in plastic surgery and many types of tissue expanders are available for the skin. The implant, approximately the size and shape of the donar area, is placed under the skin and subcutaneous tissue. If the wound tension is minimal at the time of tissue expander placement, a moderate volume of saline may be introduced without delay. This initial saline lubricates the interior of the implant and may reduce the likelihood of fold flaw erosion. The immediate introduction of saline may also place enough tension on the margins of the wound to lessen seroma and hematoma formation. Only sufficient saline should be placed at the time of implant placement to fill the dissection space without placing any undue tension on the suture line. Inflations are generally begun one or two weeks after implant placement, although inflation schedules must be individualized to the nature and anatomic location of the deformity. For practical reasons, most prostheses are inflated at weekly intervals, but highly accelerated inflation schedules have been used. Each inflation proceeds to a point of patient discomfort or blanching of the skin overlying the implant. In anesthetic regions, such as in the treatment of pressure sores, objective changes in flap vascularity should be evaluated. Although a variety of pressure transducers, oxygen tension monitors, and other types of perfusion monitoring devices are available as adjuncts to inflation of tissue expanders, objective inspection and patient response are usually used to judge appropriate implant inflation.

Skin reflectance spectroscopy has been used for measuring physiological variations in skin color and erythems. The oxyhemoglobin (amount of blood) and melanin pigment play important role in the reflection properties of skin.

Existing technologies of the related areas can be summarized in the following way: Laser speckle and holography have been used to measure small displacements of skin. However this interferometric technique has some severe technical difficulties for in-vivo use due to motion of the subject. Also a laser diffraction apparatus has been designed to measure the sarcomere length of muscle in-vivo, which is useful for tendon transfer procedures. The diffraction patterns of the striated muscle fibril due to Z dark lines have been utilized in this technique. This method will not work for skin or other soft tissues because of the lack of fine natural grating lines for laser diffraction. Soft tissue stretch is commonly measured by marking the tissue on its surface using a pen or colored tape and recording the changes in marker position with stretch. The recording device can be photographic film or video. In this method a large distance between the marked lines (Long gage length) on soft tissue is needed to reduce the experimental error in measuring the stretch. Commercially available video extensometers are rather big and can best measure flat, well-marked specimens. For in-vivo measurements, however, the curvature of the skin and other soft tissues due to natural body contours interfere with the exact measurements of the distances between the marked points.

Optical properties of biological tissues and skin are related to their structure and their chemical composition. When a beam of light reaches the skin surface, part of it will be reflected by the surface directly, while the rest will be refracted and transmitted into the skin. The direct reflection of light by a surface, where the angle of reflected light is equal of incident light, is called specular reflection, and is related only to the refractive index change between the air and reflecting medium. By nature, the reflection of light from soft tissue is diffuse rather than specular. The intensity and angular distribution of diffusion reflection is determined by transmission and scattering properties of the tissue. After diffuse reflection from the top layer of the tissue, a portion of light transmitted through the top layer and into the tissue will be scattered and absorbed by the tissue. After multiple scattering and reflection from the different layers of soft tissue, some of the transmitted light will re-emerge through the air-stratum interface into the air as part of the total reflected light intensity.

The real time measurement of the skin stretch and estimation of stresses in skin is an important problem in plastic surgery. Excessive tensile stresses delay wound healing and cause scar tissue and granulation.

OBJECTS AND SUMMARY OF THE INVENTION

The principal object of the invention is to provide an apparatus and method of noninvasively measuring stretch or deformation through light reflectivity.

Another object is to provide a portable non-contacting device to determine the stretch of an object or material, and in a particular embodiment, the skin.

One object of the present invention is to provide a device and method that utilizes changes that take place in the reflection characteristics of the object or material, such as the skin due to an applied load or stretch where the change in reflection characteristics of an object such as skin may be due to changes in the tissue roughness. A decrease in tissue roughness due to applied stretch would increase reflectivity since the object and it's surface would become more mirror-like thereby increasing the specular reflection.

It is yet another object of the present invention to provide a means to investigate or analyze different wound closure techniques, such as with a portable device according to the present invention which can measure the tension stretches around the wounds.

It is a still further object of the present invention to provide a means of analyzing the effects of different geometrical shape tissue expanders, which can create excess stress concentrations on certain regions of the skin, wherein the stretches of the skin due to tissue expanders can be followed.

Another object of the present invention is to provide an apparatus which produces a very small gage length or spot size of the light beam to enable measurement of soft tissue deformations in-vivo.

Other objects of the present invention, as well as particular features, elements, and advantages thereof, will be elucidated in, or be apparent from, the following description and the accompanying drawing figures.

The present invention achieves the above objects, among others, by providing, a method for determining the amount of stretch at a diffuse reflectance surface of an object under an applied load. The method comprises: exposing the diffuse reflectance surface of the object to an incident light beam, and measuring changes in the reflection characteristics of the diffuse reflectance surface due to the applied load. The incident light beam is focused, and further preferably is polarized. Preferably, the light beam is polarized into a desired one of the two perpendicular orientations.

The two perpendicular orientations preferably comprise a first direction wherein the incident light is polarized perpendicular to the plane of incidence (s polarization) and a second direction wherein the incident light is polarized parallel to the plane of incidence (p polarization).

The method preferably comprises polarizing at least a portion of the reflected light into one of the two perpendicular orientations.

The reflected light, or at least a portion thereof, is preferably apertured in order to define a solid angle of collected light prior to measuring changes in the reflection characteristics. The reflected light, or at least a portion thereof, is further preferably focused prior to measuring changes in the reflection characteristics.

The intensity of the incident light beam may preferably be limited, for example to achieve a substantially linear light reflection detection. The incident light beam is also preferably mechanically chopped.

A lock-in amplifier with phase sensitive detection in synch with the mechanical chopping may preferably be provided, wherein the lock-in amplifier produces a signal which is indicative of the intensity of the light reflected from the diffuse reflectance surface.

In another aspect, the present invention relates to a method for quantitatively assessing the amount of stretch induced by an applied load on an object which has a diffuse reflectance surface. The method comprises the following sequence of steps: producing a light beam; polarizing the light beam into a desired first of two perpendicular orientations which include a first orientation wherein the incident light is polarized perpendicular to the plane of incidence (s polarization) and a second orientation wherein the incident light is polarized parallel to the plane of incidence (p polarization); exposing the diffuse reflectance surface of the object to the incident chopped, polarized light beam; polarizing at least a portion of the light reflected from the diffuse reflectance surface into the desired first of the two perpendicular orientations; and detecting the intensity of the polarized, reflected light of the first orientation wherein the amount of stretch induced by the applied load on the object is correlated to the intensity of polarized reflected light.

The method further preferably comprises the following sequence of steps: polarizing the light beam into a desired second of the two perpendicular orientations; exposing the diffuse reflectance surface of the object to the incident chopped, polarized light beam of the desired second orientation; polarizing at least a portion of the light reflected from the diffuse reflectance surface into the desired second orientation: detecting the intensity of the polarized, reflected light of the second orientation; and obtaining the difference between the intensities of the polarized, reflected light at the first and second orientations wherein the amount of stretch induced by the applied load on the object is correlated to the difference in the intensities of the polarized, reflected light at the two orientations. Preferably, the incident light beam is focused.

In one preferred embodiment, the reflected light is collected at an angle which is substantially equal to the angle of incident light.

At least a portion of the reflected light is preferably apertured in order to define a solid angle of collected light prior to measuring changes in the reflection characteristics. At least a portion of the reflected light is focused prior to measuring changes in the reflection characteristics. The incident light beam is preferably mechanically chopped. A lock-in amplifier with phase sensitive detection in synch with the mechanical chopping is preferably provided, wherein the lock-in amplifier produces a signal which is indicative of the intensity of the light reflected from the diffuse reflectance surface. In one embodiment, the method according to the present invention is carried out on an object which is elastic or viscoelastic.

In yet another embodiment, the present invention comprises a method for noninvasively, quantitatively determining the amount of stretch in soft tissue under an applied load. The method comprises the following: producing a focused light beam; polarizing the light beam into a desired one of two perpendicular orientations which include a first orientation wherein the incident light is polarized perpendicular to the plane of incidence (s polarization) and a second orientation wherein the incident light is polarized parallel to the plane of incidence (p polarization); exposing the tissue to the incident chopped, polarized light beam; polarizing at least a portion of the light reflected from the tissue into the desired one of the two perpendicular orientations; aperturing at least a portion of the reflected light in order to define a solid angle of collected light; focusing at least a portion of the reflected light; and detecting the intensity of the polarized, reflected light wherein the amount of stretch induced by the applied load on the tissue is correlated to the intensity of polarized, reflected light. This sequence of steps may be repeated for the other of the two perpendicular orientations of polarization, wherein the following steps could be carried out: obtaining the difference between the intensities of the polarized, reflected light at the first and second orientations wherein the amount of stretch induced by the applied load on the tissue is correlated to the difference in the intensities of the polarized, reflected light at the two orientations.

The reflected light is preferably collected at an angle which is substantially equal to the angle of incident light. The incident light is further preferably mechanically chopped. A lock-in amplifier with phase sensitive detection in synch with the mechanical chopping is preferably provided, wherein the lock-in amplifier produces a signal which is indicative of the intensity of the light reflected from the diffuse reflectance surface.

In yet another aspect, the present invention concerns an apparatus for use in noninvasively determining the mechanical deformation at a diffuse reflectance surface of a material. The apparatus comprises: a light source for generating a light beam; means for polarizing the light beam into a desired one of two perpendicular orientations; a lens for focusing the light beam onto the diffuse reflectance surface of the material; a light analyzer means for selectively collecting light reflected from the diffuse reflectance surface and polarizing the collected light into one of the two perpendicular orientations; and light intensity measurement means for measuring the intensity of the collected, polarized light emitted from the polarization analyzer means whereby changes in light intensity provide an indication of the amount of stretch in the material.

The apparatus further preferably includes means for analyzing and comparing light intensity measurements. The apparatus may include computer means for analyzing and comparing light intensity measurements from more than one time period. The computer means may be capable of comparing the difference in light intensity measurements at the two perpendicular orientations to provide an indication of the amount of stretch in the material.

In one preferred embodiment, the light intensity measurement means comprises a light sensitive photodiode.

The two perpendicular orientations preferably comprise a first direction associated with a field which is perpendicular to the plane of incidence and a second direction associated with a field which is parallel to the plane of incidence. In a preferred embodiment, the light source is a laser. In a particular embodiment, the laser is an argon laser. The apparatus may include fiber optic cable for delivering the light beam to the diffuse reflectance surface. The apparatus also preferably includes means for mechanically chopping the light beam emanating from the light source. In one embodiment, the light beam is targeted upon the surface of the object at a desired angle of incidence. In a particular embodiment the desired angle of incidence is in the approximate range of between 20 degrees and 80 degrees.

In a preferred embodiment, the light analyzer means is positioned to collect the reflected light at an angle which is substantially equal to the angle of incidence. The light analyzer means preferably comprises an adjustable iris for aperturing the collected reflected light beam, and a lens for focusing the collected reflected light beam onto the light intensity measurement means. The apparatus also preferably includes a lock-in amplifier for measuring the light intensity incident on the reflection measurement means, such as a photodiode.

BRIEF DESCRIPTION OF THE DRAWINGS

Understanding of the present invention and the various aspects thereof will be facilitated by reference to the accompanying drawing figures, submitted for purposes of illustration only and not intended to limit the scope of the invention, in which.

DETAILED DESCRIPTION OF THE PREFERRED EMBODIMENTS

Figure 1:
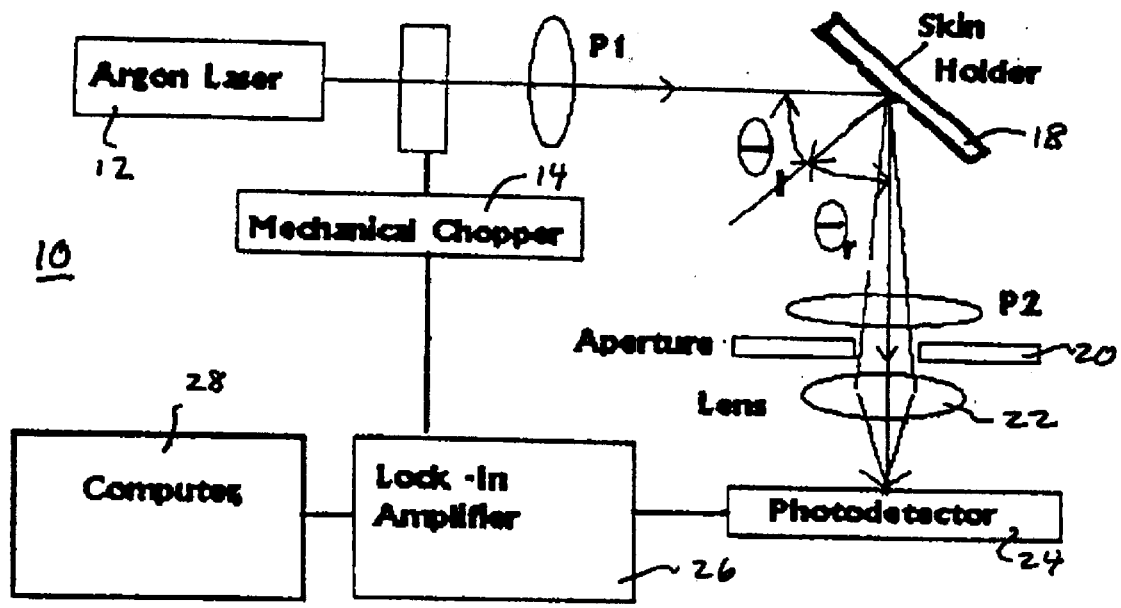
FIG. 1 is a schematic diagram of one embodiment of the present invention.

In one aspect, the present invention concerns a method for determining the amount of stretch at a diffuse reflectance surface of an object under an applied load, the method comprising: exposing the diffuse reflectance surface of the object to an incident light beam, and measuring changes in the reflection characteristics of the diffuse reflectance surface due to the applied load. The incident light beam is focused, and further preferably is polarized. Preferably, the light beam is polarized into a desired one of two perpendicular orientations.

The two perpendicular orientations preferably comprise a first direction wherein the incident light is polarized perpendicular to the plane of incidence (s polarization) and a second direction wherein the incident light is polarized parallel to the plane of incidence (p polarization).

The method preferably comprises polarizing at least a portion of the reflected light into one of the two perpendicular orientations.

The reflected light, or at least a portion thereof, is preferably apertured in order to define a solid angle of collected light prior to measuring changes in the reflection characteristics. The reflected light, or at least a portion thereof, is further preferably focused prior to measuring changes in the reflection characteristics.

The intensity of the incident light beam may preferably be limited, for example to achieve a substantially linear light reflection detection.

The incident light beam is also preferably mechanically chopped.

A lock-in amplifier with phase sensitive detection in synch with the mechanical chopping may preferably be provided, wherein the lock-in amplifier produces a signal which is indicative of the intensity of the light reflected from the diffuse reflectance surface.

In another aspect, the present invention relates to a method for quantitatively assessing the amount of stretch induced by an applied load on an object which has a diffuse reflectance surface. The method comprises the following sequence of steps: producing a light beam; polarizing the light beam into a desired first of two perpendicular orientations which include a first orientation wherein the incident light is polarized perpendicular to the plane of incidence (s polarization) and a second orientation wherein the incident light is polarized parallel to the plane of incidence (p polarization); exposing the diffuse reflectance surface of the object to the incident chopped, polarized light beam; polarizing at least a portion of the light reflected from the diffuse reflectance surface into the desired first of the two perpendicular orientations; and detecting the intensity of the polarized, reflected light of the first orientation; wherein the amount of stretch induced by the applied load on the object is correlated to the intensity of polarized, reflected light.

The method further preferably comprises the following sequence of steps: polarizing the light beam into a desired second of the two perpendicular orientations; exposing the diffuse reflectance surface of the object to the incident chopped, polarized light beam of the desired second orientation; polarizing at least a portion of the light reflected from the diffuse reflectance surface into the desired second orientation; detecting the intensity of the polarized, reflected light of the second orientation; and obtaining the difference between the intensities of the polarized, reflected light at the first and second orientations; wherein the amount of stretch induced by the applied load on the object is correlated to the difference in the intensities of the polarized, reflected light at the two orientations. Preferably, the incident light beam is focused.

In one preferred embodiment, the reflected light is collected at an angle which is substantially equal to the angle of incident light.

At least a portion of the reflected light is preferably apertured in order to define a solid angle of collected light prior to measuring changes in the reflection characteristics. At least a portion of the reflected light is focused prior to measuring changes in the reflection characteristics.

The intensity of the incident light beam is preferably limited, especially when it is desirable to achieve a substantially linear light reflection detection.

The incident light beam is preferably mechanically chopped. A lock-in amplifier with phase sensitive detection in synch with the mechanical chopping is preferably provided, wherein the lock-in amplifier produces a signal which is indicative of the intensity of the light reflected from the diffuse reflectance surface.

In one embodiment, the method according to the present invention is carried out on an object which is elastic or viscoelastic.

In yet another embodiment, the present invention comprises a noninvasive method for quantitatively determining the amount of stretch in soft tissue under an applied load. The method comprises the following: producing a focused light beam; polarizing the light beam into a desired one of two perpendicular orientations which include a first orientation wherein the incident light is polarized perpendicular to the plane of incidence (s polarization) and a second orientation wherein the incident light is polarized parallel to the plane of incidence (p polarization); exposing the tissue to the incident chopped, polarized light beam; polarizing at least a portion of the light reflected from the tissue into the desired one of the two perpendicular orientations; aperturing at least a portion of the reflected light in order to define a solid angle of collected light; focusing at least a portion of the reflected light; and detecting the intensity of the polarized, reflected light; wherein the amount of stretch induced by the applied load on the tissue is correlated to the intensity of polarized, reflected light. This sequence of steps may be repeated for the other of the two perpendicular orientations of polarization, wherein the following steps could be carried out: obtaining the difference between the intensities of the polarized, reflected light at the first and second orientations; wherein the amount of stretch induced by the applied load on the tissue is correlated to the difference in the intensities of the polarized, reflected light at the two orientations.

The reflected light is preferably collected at an angle which is substantially equal to the angle of incident light. The incident light is further preferably mechanically chopped. A lock-in amplifier with phase sensitive detection in synch with the mechanical chopping is preferably provided, wherein the lock-in amplifier produces a signal which is indicative of the intensity of the light reflected from the diffuse reflectance surface.

In yet another aspect, the present invention concerns an apparatus for use in noninvasively determining the mechanical deformation at a diffuse reflectance surface of a material. The apparatus comprises: a light source for generating a light beam; means for polarizing the light beam into a desired one of two perpendicular orientations; a lens for focusing the light beam onto the diffuse reflectance surface of the material; a light analyzer means for selectively collecting light reflected from the diffuse reflectance surface and polarizing the collected light into one of the two perpendicular orientations; and light intensity measurement means for measuring the intensity of the collected, polarized light emitted from the polarization analyzer means; whereby changes in light intensity provide an indication of the amount of stretch in the material.

The apparatus further preferably includes means for analyzing and comparing light intensity measurements. The apparatus may include computer means for analyzing and comparing light intensity measurements from more than one time period. The computer means may be capable of comparing the difference in light intensity measurements at the two perpendicular orientations to provide an indication of the amount of stretch in the material.

In one preferred embodiment, the light intensity measurement means comprises a light sensitive photodiode.

The two perpendicular orientations preferably comprise a first direction associated with a field which is perpendicular to the plane of incidence and a second direction associated with a field which is parallel to the plane of incidence.

In a preferred embodiment, the light source is a laser. In a particular embodiment, the laser is an argon laser.

The apparatus may include fiber optic cable for delivering the light beam to the diffuse reflectance surface.

The apparatus also preferably includes means for mechanically chopping the light beam emanating from the light source.

In one embodiment, the light beam is targeted upon the surface of the object at a desired angle of incidence.

In a particular embodiment, the desired angle of incidence is in the approximate range of between 20 degrees and 80 degrees.

In a preferred embodiment, the light analyzer means is positioned to collect the reflected light at an angle which is substantially equal to the angle of incidence. The light analyzer means preferably comprises an adjustable iris for aperturing the collected reflected light beam, and a lens for focusing the collected reflected light beam onto the light intensity measurement means.

The apparatus also preferably includes a lock-in amplifier for measuring the light intensity incident on the reflection measurement means, such as a photodiode.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may also be seen on other views.

With reference to FIG. 1, a preferred embodiment of an apparatus 10 according to the present invention as shown in FIG. 1 which was used for testing of various specimen samples includes an argon laser 12 used as a light source. The light from the light source is directed at skin and redirected off the skin by diffuse reflection. The reflected light is then measured at selected points to determine the diffuse reflectance of the light. Where diffuse reflectance is defined as the ratio of the flux leaving a surface or medium by diffuse reflection to the incident flux. The measurement of the diffuse reflectance may require sensitive measurement of the reflected light. To achieve such sensitive measurements a noise suppression circuit is used to improve the quality of the measurement. It will be appreciated by those skilled in the art that a number of noise suppression techniques may be implemented and as such, the configuration of the noise suppression circuit may vary. The noise suppression circuit of the preferred embodiment includes a mechanical chopper 14. The laser light is mechanically chopped by a mechanical chopper 14. The chopped laser light beam is then polarized by polarizer P1. Skin is mounted on a skin holder 18. Polarized light with a small spot size is reflected from the surface of the skin and is collected from the specular direction where the reflected light was polarized by polarizer P2. The polarized, collected light is then passed through an aperture 20 and lens 22. The collected light is detected with a light sensitive photo diode 24. The noise suppression circuit further includes a lock-in amplifier that cooperates with the mechanical chopper 14 to attain the sensitive measurement. Using the noise suppression circuit of the preferred embodiment, light measurements are taken in the form of discrete samples of measured light. The sampling rate corresponds to the rate of the mechanical chopper in which several discrete samples are taken and locked-in by the locking amplifier to form a single measurement. The discrete sampling serves to suppress noise formed by ambient light and multiple reflections of the light from the light source. As an added benefit of the noise suppression circuit in which discrete sampling is implemented, the mechanical chopper reduces the exposure time that the light from the light source is directed at the skin. Polarization of the analyzer is settable in one of two perpendicular orientations. The change in light intensity between the two perpendicular polarization measurements of the analyzer is related to the amount of stretch in the skin which in turn corresponds to the amount of stress experienced by the skin.

The polarized laser light with a small spot size which has a light intensity lower than the damaged level of tissues is reflected from the skin. The reflected light is generally collected from the specular direction using a lens 22 after the light passes through a polarization analyzer. The light is detected using a light sensitive photodiode 24. Polarization of the analyzer is selectively set in one of two perpendicular directions. Experiments using this method and apparatus have shown that the change in light intensity between the two perpendicular orientations of the polarization analyzer is related to the amount of stretch. This change in reflection characteristics of an object such as skin may be due to changes in the tissue roughness. A decrease in tissue roughness due to applied stretch would increase reflectivity since the object and it's surface would become more mirror-like thereby increasing the specular reflection. It will be appreciated that materials other than skin may be tested to determine the affects of stress on such objects.

As discussed below, initial measurements by using the argon laser gave very good correlation between the stretch along the Langer's lines of the test skin and change in light intensity, and the stretch perpendicular to the Langer's lines gave inconclusive results.

Experiment I

In preliminary measurements, two different wavelengths (458 nm and 632.8 nm) of light were used. In all measurements, the angle of incidence ($E_i$) was varied from roughly 20 degrees to 70 degrees. In each measurement, reflected light in the specular direction was analyzed. The reflected light was collected with a 35 mm focal length lens 22 and focused onto a Si photodiode detector 24 functioning as an optical sensor. Due to the diffuse nature of the reflected light, a 1 cm aperture 20 was placed next to the lens 22 to define the solid angle of collected light. The light intensity was kept low enough to ensure a linear detector response (voltage proportional to laser power). The laser power was detected by mechanically chopping the incident laser light and utilizing a lock-in amplifier 26 with phase sensitive detection. The polarization of the incident light was varied using polarizer P1. The incident light was polarized either parallel to the plane of incidence (s polarization) or perpendicular to the plane of incidence (p polarization). the analyzing polarizer P2 selects either the s or p polarization of the reflected light. As a function of the stretch of the test sample such as skin, the s and p components of the reflected light were measured for both polarizations of incident light. A computer 28 was used for data acquisition, which preferably includes the capability of comparing the difference in light intensity measurements at the two perpendicular orientations to provide an indication of the amount of stretch in the material, and analyzing and comparing light intensity measurements from more than one time period. The computer means may additionally serve as a control means for one or more of the other elements of the apparatus 10. Experiments on guinea pig skin showed that the change in the intensity of the reflected light when skin is stretched along the Langer's lines was proportional to the stretch of the skin. The Argon laser with 458 nm wavelength with about 70 degrees of angle of incidence gave the best results. It is believed that laser light with a wavelength of less than 600 nm provide good results. Guinea pig skin was used as it presents characteristics similar to human skin. For purposes of such experiments, it will be appreciated by those skilled in the art that such results are applicable to human skin.

Figure 2:
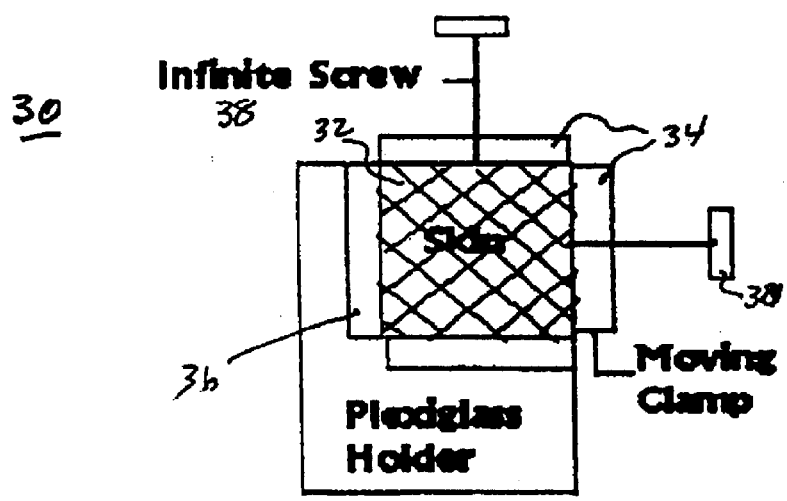
FIG. 2 is a schematic diagram of a test apparatus for applying a stretch load to a specimen.

As depicted in FIG. 2, testing was performed on a guinea pig skin. A simple device 30 was built to apply stretch to the skin pieces. Four sides of the rectangular skin sample 32 were clamped on this Plexiglas stretch device 30. Two adjacent clamps 34 were movable with respect to the Plexiglas plate 36 by infinite screws 38. The skin 32 was held on the Plexiglas piece by two adjacent plastic pieces which were 90 degrees to each other. The plastic pieces were attached to the Plexiglas piece by thumb screws. Skin 32 was placed on a 3.5 inch by 3.5 inch area. The middle part of the Plexiglas plate 36 was covered with a dull (non-shining) black thin plastic piece. This plastic piece eliminated any reflection from the Plexiglas surface. Reflections from several skin pieces were examined. Four guinea pig skin samples were obtained from an outside source (Hartley Guinea pigs, 500 to 550 gram) (Buckshire Corporation, Perkasie Pa.). The samples were shaved and delivered in saline solutions on the same day after the animals were sacrificed. The Langer's lines in guinea pigs are parallel to their spine structure. The skin pieces were arranged such that the Langer's lines were always parallel to the one side of the stretching device 30. Skin was stretched in one direction, then back to the original position. Subsequently, the skin was stretched in the other direction (perpendicular to the first direction) and then back to the original position. The order of stretch directions along the Langer's lines and perpendicular to the Langer's lines alternated from one experiment to the next experiment to eliminate any bias behavior that could set during the first measurement due to viscoelastic behavior of the tissue. The skin was rested for 5 to 10 minutes between the measurements. The skin was kept wet with saline solution during the experiments.

Due to the preliminary nature of the simple skin holder device 30, stretch in one direction did not create a uniform deformation along that direction because the other sides of the skin parallel to the stretch direction were also clamped and could not follow the deformation uniformly. The central part of the skin which was used in the experiments was subjected to somewhat uniform deformation field parallel to the stretch direction. During the measurements, laser light was reflected in somewhat uniform deformation field parallel to the stretch direction. During the measurements, laser light was reflected in the central portion of the skin. Different amounts of stretch were applied to the samples, up to one-half inch. The infinite screw was turned between the measurements by hand (one-eighth of an inch or one-fourth of an inch). Some viscoelastic deformation were set during the experiments. After the maximum stretch was reached, the skin was returned to the original position with the same protocol. Typically, the skin did not recover the original position because of the viscoelastic deformations and because of the friction between the Plexiglas surface and the skin, although this surface was kept wet with saline solution.

Figure 3:
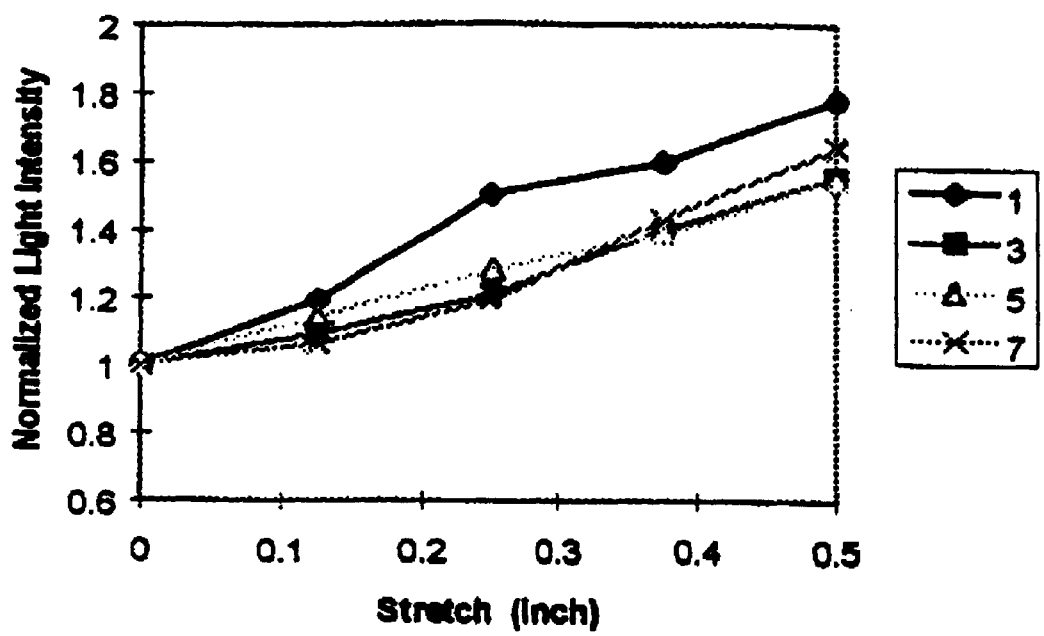
FIG. 3 is a graphical illustration of experimental measurements of normalized light intensity versus stretch, for stretch parallel to the Langer's lines of the skin tested.

As illustrated in FIG. 3, experiments with Argon laser showed that the stretches applied parallel to the Langer's lines gave almost a linear relation between the stretches and light intensity. Light intensity was computed by taking the difference between two perpendicular measures of the analyzer. In FIG. 3, the light intensities were normalized by dividing by the unstretched intensity. The linear correlation between the applied stretch and the light intensity suggests successful application of uniform stretch in the central portion of the skin, where measurements were made.

Figure 4:
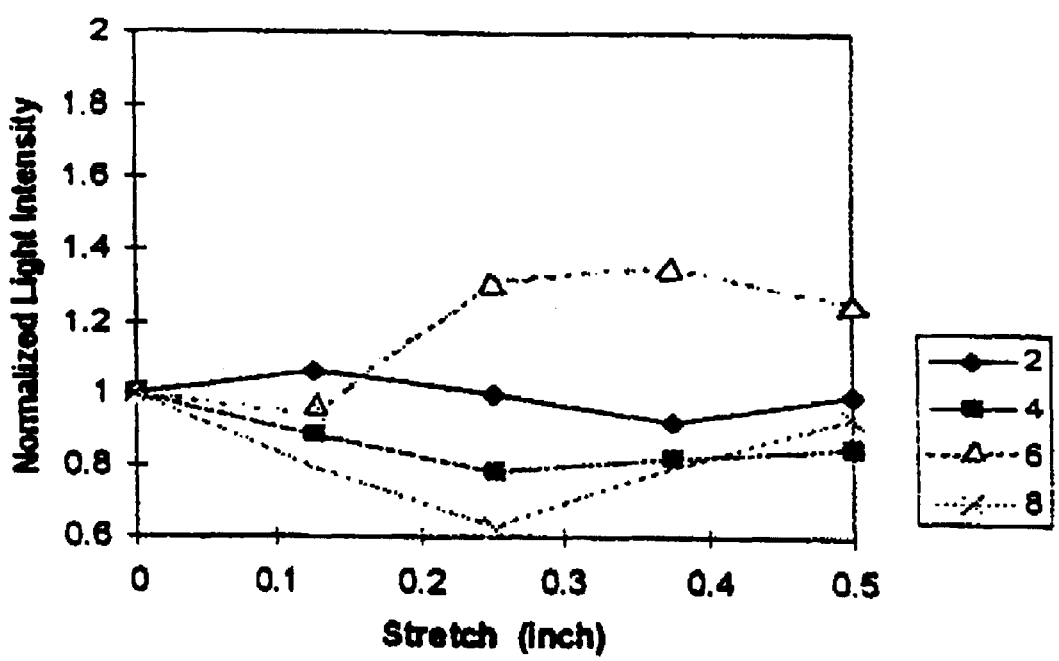
FIG. 4 is a graphical illustration of experimental measurements of normalized light intensity versus stretch, for stretch perpendicular to the Langer's lines of the skin tested.

FIG. 4 shows the stretch versus light intensity when samples were stretched perpendicular to the Langer's lines. The results on four samples show that the light intensity is independent of the stretch in this direction.

Initial experiments on skin samples in-vitro using an Argon laser light source showed that stretches applied parallel to the Langer's lines (Langer's lines described as the natural tension lines that exist in the skin) gave almost a linear relation between stretch and light intensity.

In another series of experiments, polymers were tested on an embodiment of the present invention. In order to test the polymers, the sample holder was modified: two micrometers were placed next to each other separated by a 50 mm gap. Samples were clamped onto the micrometers. The other sides of the samples were either left free or clamped onto the holder. When the heads of the micrometers moved with respect to each another by an equal amount, the center portion of the sample stayed at the same position. Thus, a uniform tension field was created at the center of the sample where the polarized light was reflected, especially for the case of four sided clamped samples. A 488 nm argon ion laser was used at an angle of incidence and reflection of about 40 degrees.

Figure 5:
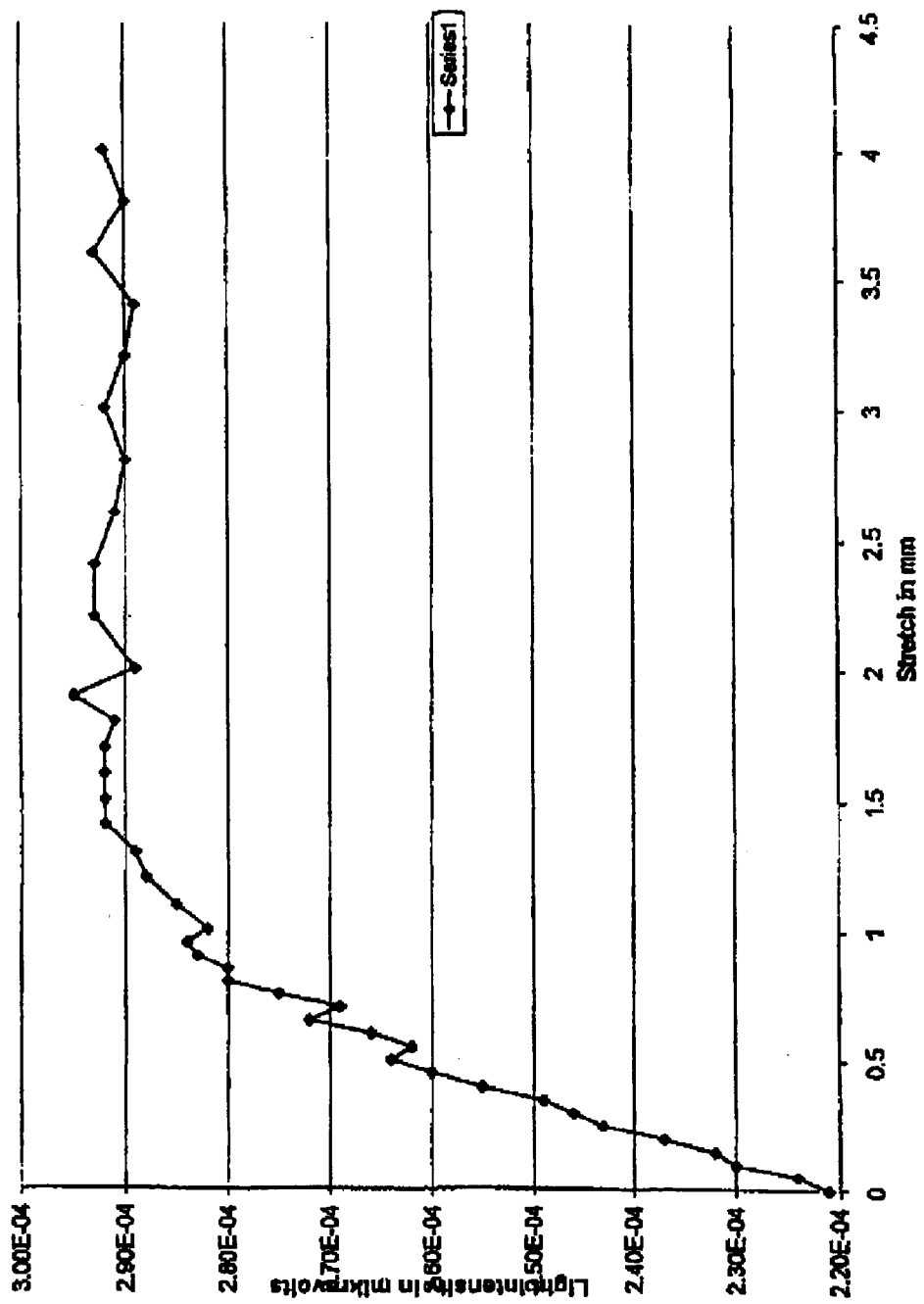
FIG. 5 is a graphical illustration of experimental measurements of light intensity versus stretch, for stretch in a medium modulus natural latex material obtained from a powder free glove cuff.
Figure 6:
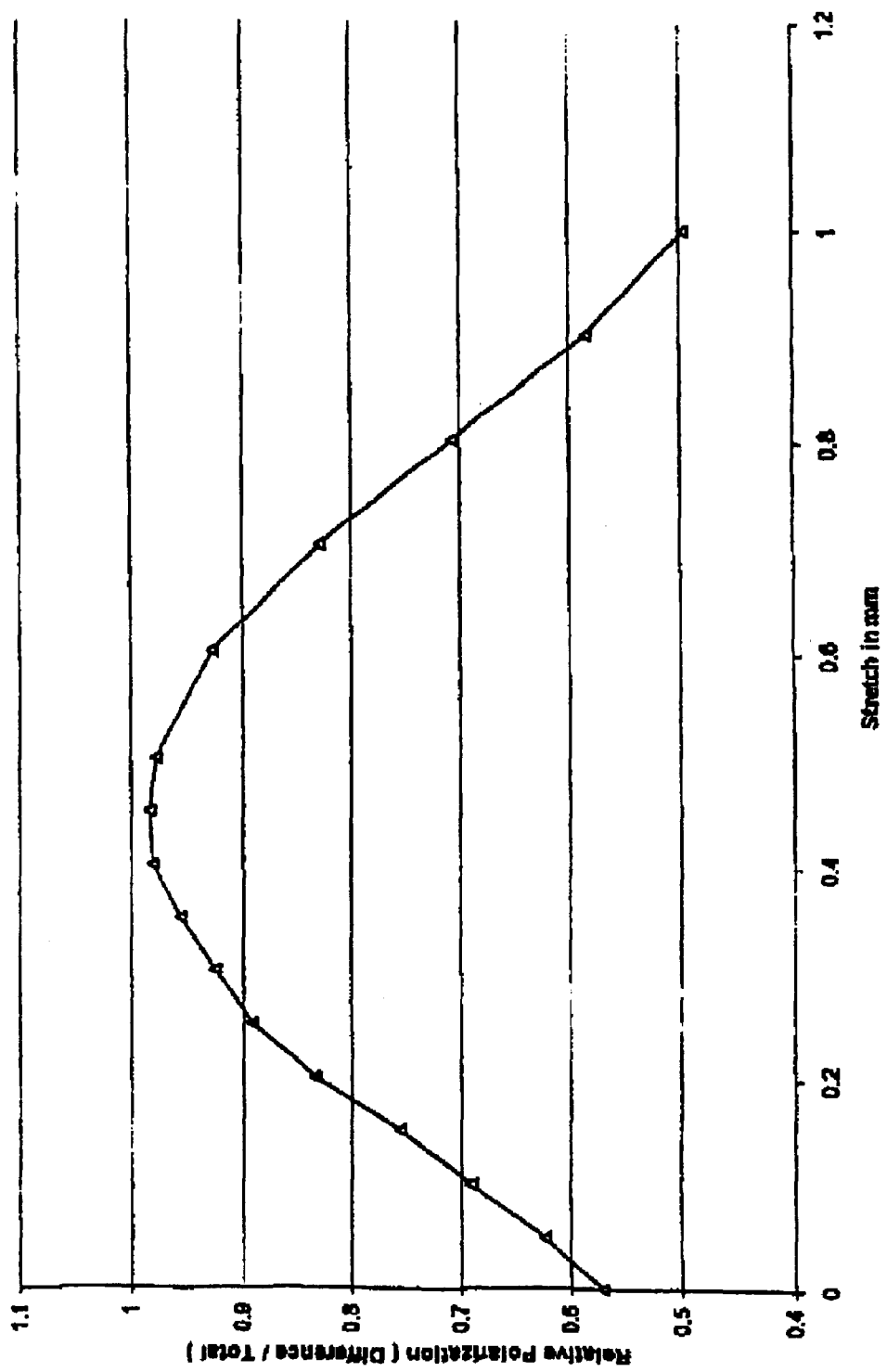
FIG. 6 is a graphical illustration of experimental measurements of light intensity versus stretch, for stretch in a photoelastic polycarbonate sheet material.

Measurements of the stretch in the polymer films are illustrated in FIGS. 5–6, as described below.

FIG. 5 illustrates the testing of medium modulus natural latex (taken from a powder free glove cuff) having a thickness of 0.17 mm which shows a linear type relationship between the total light intensity, obtained by adding 90 degrees reflected light to the 0 degrees reflected light and the applied stretch. Samples were clamped from four sides. A linear relationship was obtained for almost up to 1 mm of stretch, corresponding to 2% strain. Further stretch of the sample, up to 4 mm (8% strain) showed saturation after approximately 1.3 mm stretch. Thus, these experimental results showed a very good linear relation between a latex base material and reflected total light intensity for strains up to 2%.

FIG. 6 shows test results for a photoelastic or birefringent polycarbonate sheet material having a thickness of 0.5 mm and obtained from Measurement Group Inc. of Raleigh, N.C. Type PS-4D. The material was clamped only onto the micrometers, i.e. only on two sides.

FIG. 6 shows the ratio (relative polarization) of light intensity difference (90 degrees reflected light minus 0 degrees reflected light) to the total intensity (0 degrees reflected light plus 90 degrees reflected light). A parabolic relationship was obtained for up to 1 mm stretch (2% strain), indicating that the birefringent material used provided a nonlinear relationship between the applied stretch and relative polarization. Thus, as compared to the linear relationship (of total power versus stretch) that was observed in skin samples where the stretch was parallel to the Langer's lines and in latex samples, birefringent polycarbonates showed a parabolic relation between relative polarization versus stretch.

Experiment II

Figure 7:
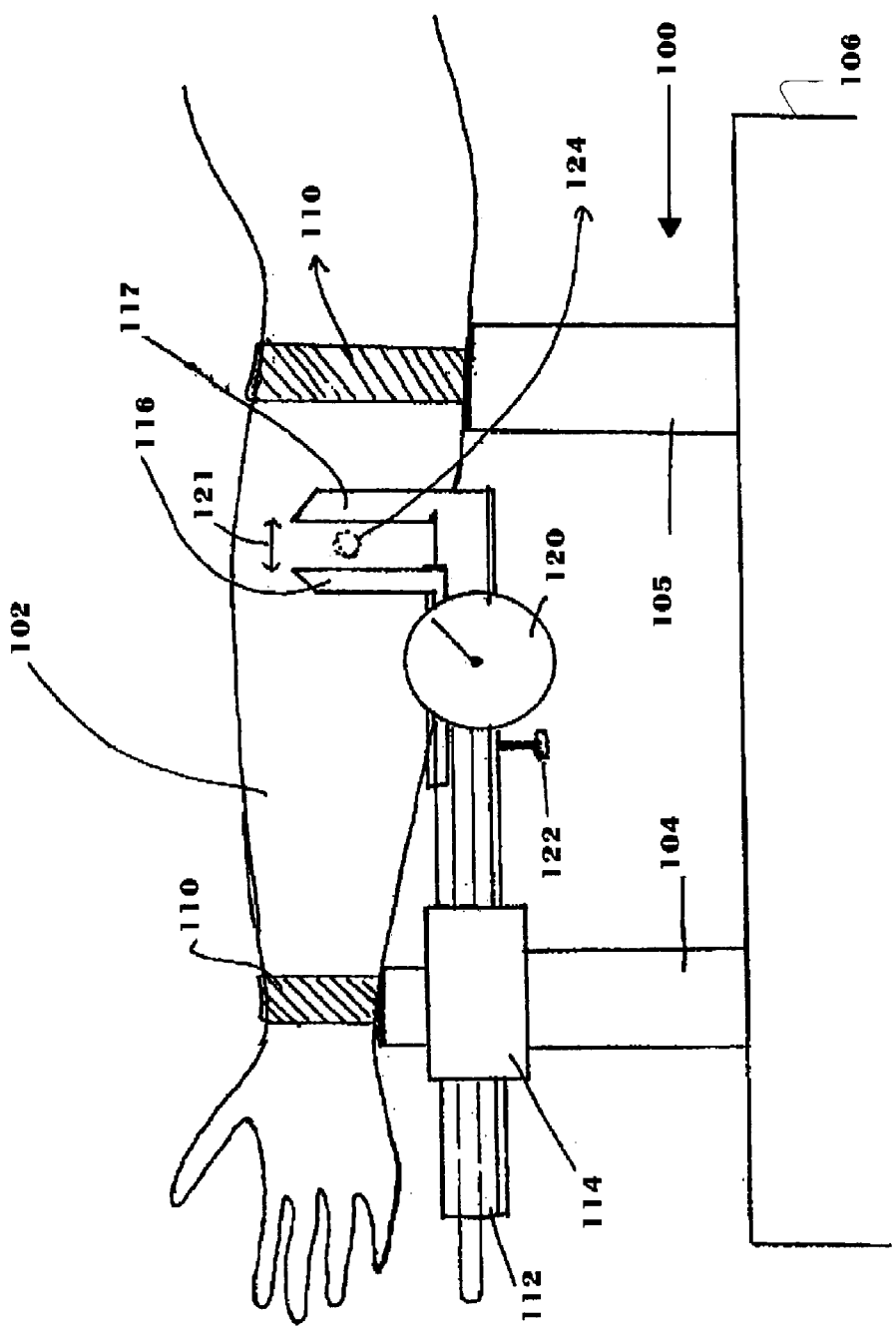
FIG. 7 is a schematic diagram of an apparatus for the measurement of the human skin.
Figure 8:
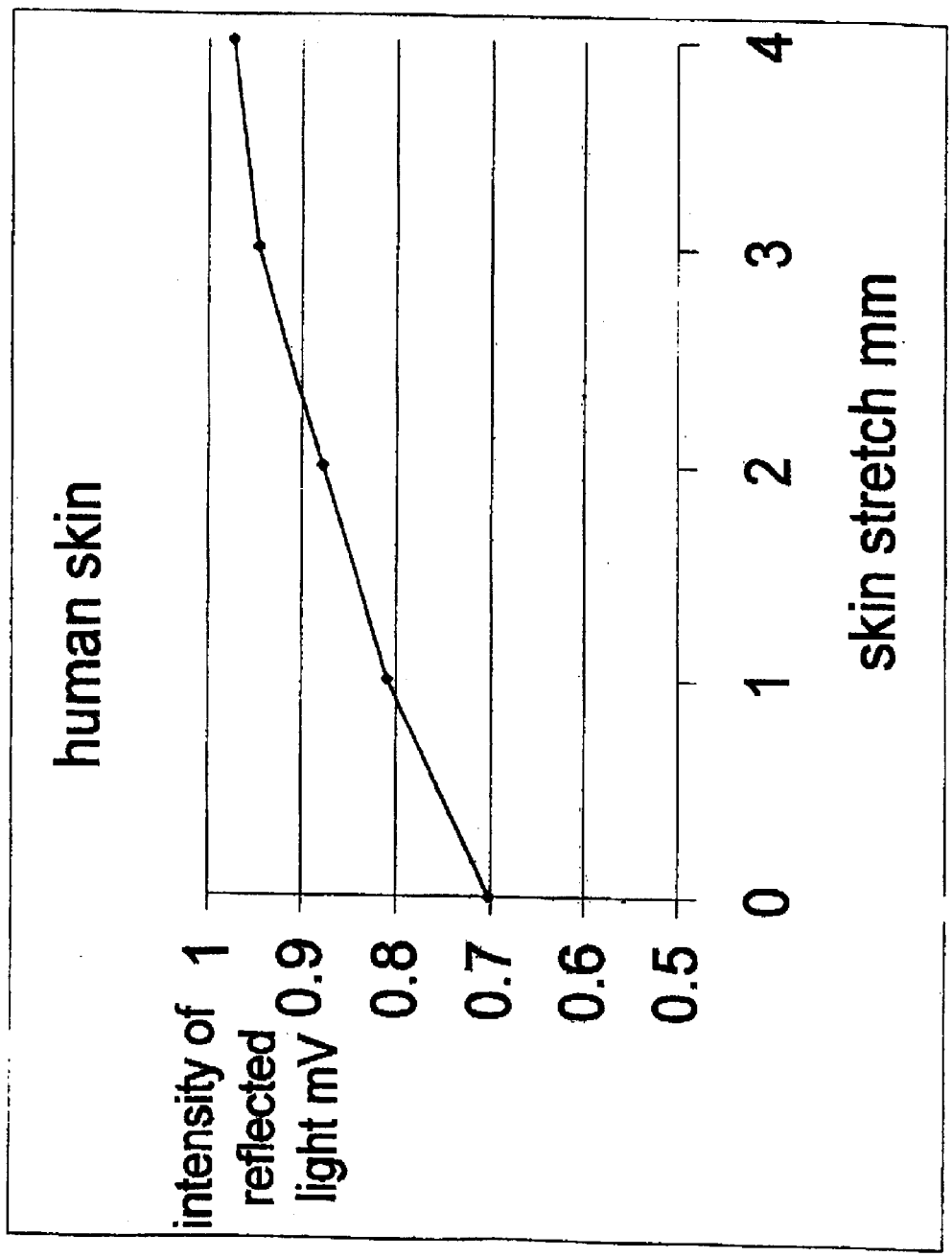
FIG. 8 is a plot correlating light intensity to skin stretch for measuring human tissue.

In a second experiment (FIG. 7) the process of the present invention was used on human skin in-vivo. In this measurement, an armrest 100 for the right forearm 102 was used. The forearm is supported with two plastic supports 104–105 vertically extending from a table 106 or other flat surface. One support 104 is located near the wrist and a second support 105 is located near the elbow. The supports 104–105 are movably placed in spaced apart relation and adjusted to generally underlie the wrist and elbows. The height of the wrist support 104 is slightly lower than the elbow support 105 to elevate the wrist to a more comfortable position in relation to the elbow. The arm is secured by velcro straps 110 on the supports. A micrometer 112 is secured by a clamp 114 to the armrest and extends along the length of the length of the forearm. The measuring side of the micrometer includes two legs 116–117, where objects are placed in between for measurements. The legs 116–117 were placed against the skin at the anterior side of the forearm 102. Two legs 116–117 were adjusted to create a 20 mm opening there between and were attached to the skin of the forearm with Scotch™ brand double tape. Preferably any double tape or adhesion means may be used so long as it resists detachment during skin stretching, but allows for relatively painless removal from the forearm when stretching has been completed. Using the same technique which is summarized above in Experiment I the intensity of the parallel (p) and perpendicular (s) reflected light intensities were measured at a point 124 on the arm. The differences of the reflected light intensities were plotted against the additional opening 121 to the initial gage length (20 mm). Skin was stretched with the micrometer by moving one leg against the other monitored by a dial gage 120. After each additional opening, the moving leg was locked with its own set screw 122 before the optical measurement. The direction of the stretch was along the lengthwise axis of the forearm. The difference between the intensities of light versus different additional openings were plotted as illustrated by FIG. 8 (1, 2, 3 and 4 mm additional openings were used). With described armrest, a very good correlation between the additional openings and the intensity difference of the reflected polarized lights for human skin in-vivo was found.

Thus, useful results have been experimentally obtained by the present invention for biological tissues and polymers.

It may be desirable, especially for a particular embodiment of the present invention and/or for a particular application or material or object to be analyzed or measured, to optimize wave length of the light source, angle of incidence, polarization and/or the spot size of the incident light. Additional in-vitro skin stretch experiments, for example, could be used to optimize these parameters and measure the mechanical properties of the skin.

The performance of a particular embodiment of the present invention may depend on wavelength due to a dependence on transmission/adsorption of biological tissues or artificial materials and other components which are intimately related to the main structure (e.g. in the case of biological tissues, the effect of blood).

The angle of incidence can be varied between 0 and 90 degrees. An optimum incident angle or range of incident angles may be desirable for a particular embodiment and/or with a particular test specimen.

The polarization of the incident light partially determines the depth of penetration of the light as can be shown by considering the electromagnetic properties of light. The relative reflection of both s and p (electric field perpendicular and parallel to the plane of incidence, respectively) incident light could be measured and correlated to the tension directions in the biological tissues or other materials as well as the angle of incidence.

The spot size of the incident light on the material or object being measured could be varied e.g. between several millimeters (unfocused laser beam) to tens of micrometers (focused laser beam). It is expected that the topology of biological tissues (and concomitantly the reflectance) can change significantly over these spatial scales, and accordingly may have a corresponding effect on the reflectance and correlation with tissue tension.

The present invention, by analyzing the change in the diffuse reflectance properties of skin due to mechanical deformation can be used to determine soft tissue deformations noninvasively. For example, surgeons will be able to discern stretches of soft tissues in real time with ease due a sufficiently small spot size. Measuring the tension in wound closures and skin flaps will help surgeons to treat patients more successfully with a minimum of scar tissue. The present invention will also help surgeons to use tissue expanders more effectively to treat burn and accident patients by knowing how much they can stretch skin in each step safely with the tissue expander. This will help surgeons to treat patients successfully in a short period of time.

A post-operatively adjustable saline filled tissue expander could be used to create a tissue expansion in an animal model. Initial and subsequent changes in the stretches of the skin (due to progressively larger-saline fill) could be monitored by an optical device for correlation purposes. In order to measure the soft tissue stretch over an area of tissue, two embodiments for an optical sensor are possible. In the first technique (point-to-point measurement), the invention as described includes an optical sensor in the form of a photodiode detector to be scanned over the tissue surface. At each point on the tissue surface, a measurement would be made. From this point to point scan, the soft tissue stretch as a function of position on the tissue surface could be determined. An alternative would be to replace the photodiode detector with an array of photodetectors (eg. CCD camera). The camera and lens would be positioned in order to image the illuminated surface onto the detector array. Using the same polarization measurements as described previously, one could then generate a two-dimensional image of the soft tissue stretch. The second technique will improve the functionality of the invention: (1) it takes less time to acquire the data via imaging to an array of detectors compared to a point-to-point method. (2) A 2-D image of the stress in an area of tissue gives more information to the surgeon or medical practitioner than does a single point measurement.

Thus, by monitoring changes in the reflected light due to the skin stretch, the present invention can provide a noninvasive, in-situ, real-time, in-vivo diagnostic tool for measuring stretch such as skin stretch.

All of the optical components of the present invention can be miniaturized to fit into a portable 1 cm$^3$ prototype device. Laser light can be coupled into a device utilizing fiber optic cables, thereby increasing its portability during surgery. The light will be focused onto the skin tissue thereby ensuring a small spot size and gage length.

Different wound closure techniques can be investigated with the present invention by measuring the tension stretches around the wounds, thereby providing valuable information to the surgeon during surgery.

Different geometrical shape tissue expanders can create excess stress concentrations on certain regions of the skin. With the present invention, the stretches of the skin due to tissue expanders can be followed. Every point of the skin above the tissue expanders can be quickly monitored by the present invention. Also the changes which take place in the stretch patterns of the skin over time after each fill can be monitored. Thus, the present invention can supply additional information to the surgeons for deciding the schedule of the fills and the amount of the fill at each time, thereby reducing complications from skin expansion, such as tissue necrosis, implant exposure and infection, and thereby improving the outcome of the surgery and shortening the treatment time.

The present invention, by analyzing the change in the diffuse reflectance properties of skin due to mechanical deformation, can be used to determine soft tissue deformations noninvasively. A small spot size (gage length) with a miniaturized detector with fiber optic technology will allow surgeons to determine the stretch of the soft tissues in real time with ease. This will add another tool for surgeons to make good judgment during the surgery. The present invention will be very useful especially in plastic surgery because of the effect of tension forces in the outcome of a successful surgery. The present invention will also be used in mechanical experiments to determine the deformation of the diffuse reflectance materials as a non-contacting extensometer. With a very small spot size (gage length) the present invention could be superior to the existing technology of video extensometers. Determining mechanical properties of soft tissues and obtaining also the mechanical properties of soft artificial biomaterials can be very important to the field of biomechanics and biomaterials.

A portable soft tissue stretch measuring device according to the present invention will be a very useful tool especially for the plastic surgeons. Measuring the tension in wound closures, skin flaps and in tissue expanders will help the surgeons to treat patients more successfully with minimum scar tissue and increase the speed of treatment especially after the accidents and burns by knowing how much they can stretch skin each step for speeding the treatment. Also it can be used to determine the excess mechanical deformations of the walls of internal vessels or internal organs around the surgical site during the surgery. Thus, useful information could be gained by the surgeon to avoid tissue injury during surgery by applying right amount of force with suturing.

Thus, the present invention can give instant information on the stress concentration of tissues due to different surgical procedures, and can be used to correlate the measured stretches of the skin with its viability and the amount of scar tissue formation in wound closure models and in tissue expanders. The present invention may help the surgeons to determine the amount of the correct filling and the frequency of filling of the tissue expanders and also will give guidance during the tissue expansion surgeries where the excessive tensile stresses delay wound healing and cause scar tissue. The present invention may be used intraoperatively to assess the flexibility of a primary closure of a wound, viability of a skin flap or expanded skin; thereby assisting the surgeon in making crucial decisions during the surgery. Presently the surgeons rely only on subjective assessment derived from experience so objective data will be extremely helpful.

The present invention may be used to measure stretches in other tissues besides skin (e.g. blood vessels, corneal tension for glaucoma). The stretches in tissues below the skin surface can be measured during surgery (e.g. strain in heart valves, connective tissue structures). A portable device with a very small probe and a penetrable tip according to the present invention can also be used to determine mechanical response which may retard wound healing. Also the present invention can be used in the high stress regions deformations prior to the failure of mechanical devices, such as internal and external prosthetics, bone tissue etc., as well as tissues below the skin. High tension stresses (large deformations) after wound closure contribute to enhanced scar tissue, and the present invention may be utilized to find the high stress regions, thereby allowing the surgeons to decide on an optimum wound closure geometry. Animal experiments with different wound openings can be conducted where measurements of the amount of scar tissue can be related to the geometry of the wounds, and measuring the stretches with the present invention can provide an addition information which will be useful to plastic surgeons to decide on an optimum wound closure geometry which will create minimum scar tissue.

The present invention can provide a noninvasive, in-situ, real-time, in-vivo diagnostic tool for measuring skin stretch for plastic surgeons by monitoring change in the reflected light intensity due to the skin stretch.

In a preferred embodiment, the present invention is constructed from optical components which can be miniaturized to fit into a portable (e.g. 1 cm$^3$) device or probe. Laser light can be coupled into the device using fiber optic cables thereby increasing its portability during surgery in other applications. The light can be focused on the skin or on any other material thereby ensuring a small spot size and gage length.

According to the present invention, the change in the diffuse reflectance properties of biological tissues due to mechanical deformation can be used to determine soft tissue deformations noninvasively. A small spot size (gage length) with a miniaturized detector with fiber optic technology will allow surgeons to determine the stretch of soft tissues in real time with ease. This is an important point in plastic surgery, because the large stretches around the wounds which generate high stresses cause scar tissue and granulation. The present invention will help to minimize scarring and granulation and improve the outcome of the surgery. Moreover, surgeons will be able to get instant information about the amount of stretch of soft tissue during surgery.

The present invention can also be used in mechanical experiments to determine the deformation of diffuse reflectance materials as a non-contacting extensometer. With a very small spot size (gage length) the present invention could be superior to the existing technology of video extensometers. Determining mechanical properties of soft tissues and obtaining the mechanical properties of soft artificial biomaterials can be very important to the field of biomechanics, biomaterials and material science.

Thus, one medical application of this technique will be a portable soft tissue stretch measuring device which will be a very useful tool especially for the plastic surgeons. Measuring the tension in wound closures, skin flaps and in tissue expanders will help surgeons to treat patients more successfully with minimum scar tissue and increase the speed of treatment, especially after accidents and burns. Some of the other applications of the technique in the medical field also include determining the excess mechanical deformations of the walls of internal vessels or internal organs around the surgical site during surgery. Furthermore, the present invention could provide useful information for the surgeon to avoid tissue injury during surgery by applying the proper amount of force with suturing.

Other medical applications of the present invention will be useful, for example, in determining the orientation of fibers prior to surgery which is important for areas such as the sternum where Langer's lines are not clearly delineated and scarring is a clinical problem. Furthermore, in soft tissue mobilization and massage there is little instrumentation available to document changes in soft tissue properties with such treatment, so that the present invention may allow identification of areas of soft tissue tension that require treatment and allow the physician to monitor the results of such treatment.

The present invention can also be used for rapid in-situ testing of elastic/viscoelastic properties of materials such as in a plastics or manufacturing facility, for example a plastic which is used as artificial skin for skin replacement. The present invention may also be useful in characterizing the elastic/viscoelastic properties of the artificial skin either during the manufacturing process (on-line factory monitoring) or after the artificial skin has been manufactured. For example, in plastic manufacturing, as the films are being stretched after exiting a die on the factory floor, the present invention could provide real-time diagnostic which can then be used to control the manufacturing process.

It should be understood that the present invention is not limited to the medical field, and can be utilized in other areas as well, such as in industrial settings and materials research.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method for determining the amount of stretch at a diffuse reflectance surface of an object under an applied load, the method comprising:

exposing the diffuse reflectance surface of the object to an incident light beam; and measuring changes in the reflection characteristics of the diffuse reflectance surface due to the applied load.

2. The method according to claim 1 further comprising focusing the incident light beam.

3. The method according to claim 1 further comprising polarizing the incident light beam.

4. The method according to claim 3 wherein said light beam is polarized into a desired one of two perpendicular orientations.

5. The method according to claim 4 wherein said two perpendicular orientations comprise a first direction wherein the incident light is polarized perpendicular to the plane of incidence (s polarization) and a second direction wherein the incident light is polarized parallel to the plane of incidence (p polarization).

6. The method according to claim 4 further comprising polarizing at least a portion of the reflected light into one of said two perpendicular orientations.

7. The method according to claim 1 further comprising aperturing at least a portion of the reflected light in order to define a solid angle of collected light prior to measuring changes in the reflection characteristics.

8. The method according to claim 1 further comprising focusing at least a portion of the reflected light prior to measuring changes in the reflection characteristics.

9. The method according to claim 1 further comprising limiting the intensity of the incident light beam.

10. The method according to claim 1 further comprising mechanically chopping the incident light beam.

11. The method according to claim 10 further comprising providing a lock-in amplifier with phase sensitive detection in synch with the mechanical chopping, wherein said lock-in amplifier produces a signal which is indicative of the intensity of the light reflected from the diffuse reflectance surface.

12. A method for quantitatively assessing the amount of stretch induced by an applied load on an object which has a diffuse reflectance surface, the method comprising the following sequence of steps:

producing a light beam;

polarizing the light beam into a desired first of two perpendicular orientations which include a first orientation wherein the incident light is polarized perpendicular to the plane of incidence (s polarization) and a second orientation wherein the incident light is polarized parallel to the plane of incidence (p polarization);

exposing the diffuse reflectance surface of the object to the incident chopped, polarized light beam;

polarizing at least a portion of the light reflected from the diffuse reflectance surface into the desired first of said two perpendicular orientations; and detecting the intensity of the polarized, reflected light of the first orientation;

wherein the amount of stretch induced by the applied load on the object is correlated to the intensity of polarized, reflected light.

13. The method according to claim 12 further comprising the following sequence of steps:

polarizing the light beam into a desired second of said two perpendicular orientations;

exposing the diffuse reflectance surface of the object to the incident chopped, polarized light beam of the desired second orientation;

polarizing at least a portion of the light reflected from the diffuse reflectance surface into the desired second orientation;

detecting the intensity of the polarized, reflected light of the second orientation; and obtaining the difference between the intensities of the polarized, reflected light at the first and second orientations;

wherein the amount of stretch induced by the applied load on the object is correlated to the difference in the intensities of the polarized, reflected light at the two orientations.

14. The method according to claim 12 further comprising focusing the incident light beam.

15. The method according to claim 12 further comprising collecting the reflected light at an angle which is substantially equal to the angle of incident light.

16. The method according to claim 12 further comprising aperturing at least a portion of the reflected light in order to define a solid angle of collected light prior to measuring changes in the reflection characteristics.

17. The method according to claim 12 further comprising focusing at least a portion of the reflected light prior to measuring changes in the reflection characteristics.

18. The method according to claim 12 further comprising limiting the intensity of the incident light beam.

19. The method according to claim 12 further comprising mechanically chopping the incident light beam.

20. The method according to claim 19 further comprising providing a lock-in amplifier with phase sensitive detection in synch with the mechanical chopping, wherein said lock-in amplifier produces a signal which is indicative of the intensity of the light reflected from the diffuse reflectance surface.

21. The method according to claim 12 wherein the object is elastic or viscoelastic.

22. The method according to claim 12 wherein said object is biological or non-biological.

23. A method for noninvasively, quantitatively determining the amount of stretch in soft tissue under an applied load, the method comprising:
   producing a focused light beam;
   polarizing the light beam into a desired one of two perpendicular orientations which include a first orientation wherein the incident light is polarized perpendicular to the plane of incidence (s polarization) and a second orientation wherein the incident light is polarized parallel to the plane of incidence (p polarization);
   exposing the tissue to the incident chopped, polarized light beam;
   polarizing at least a portion of the light reflected from the tissue into the desired one of said two perpendicular orientations;
   aperturing at least a portion of the reflected light in order to define a solid angle of collected light;
   focusing at least a portion of the reflected light; and
   detecting the intensity of the polarized, reflected light;
   wherein the amount of stretch induced by the applied load on the tissue is correlated to the intensity of polarized, reflected light.

24. The method according to claim 23 further comprising repeating the sequence of steps in claim 23 for the other of said two perpendicular orientations of polarization, and further comprising:
   obtaining the difference between the intensities of the polarized reflected light at the first and second orientations;
   wherein the amount of stretch induced by the applied load on the tissue is correlated to the difference in the intensities of the polarized, reflected light at the two orientations.

25. The method according to claim 23 further comprising collecting the reflected light at an angle which is substantially equal to the angle of incident light.

26. The method according to claim 23 further comprising mechanically chopping the incident light beam.

27. The method according to claim 26 further comprising providing a lock-in amplifier with phase sensitive detection in synch with the mechanical chopping, wherein said lock-in amplifier produces a signal which is indicative of the intensity of the light reflected from the diffuse reflectance surface.

28. An apparatus for use in noninvasively determining the mechanical deformation at a diffuse reflectance surface of a material, the apparatus comprising:
   a light source for generating a light beam;
   means for polarizing the light beam into a desired one of two perpendicular orientations;
   a lens for focusing the light beam onto the diffuse reflectance surface of the material;
   a light analyzer means for selectively collecting light reflected from the diffuse reflectance surface and polarizing the collected light into one of said two perpendicular orientations; and
   light intensity measurement means for measuring the intensity of the collected, polarized light emitted from said polarization analyzer means;
   whereby changes in light intensity provide an indication of the amount of stretch in the material.

29. The apparatus according to claim 28 further comprising means for analyzing and comparing light intensity measurements.

30. The apparatus according to claim 28 further comprising means for analyzing and comparing light intensity measurements from more than one time period.

31. The apparatus according to claim 30 wherein said analyzed computing means is capable of comparing the difference in light intensity measurements at said two perpendicular orientations to provide an indication of the amount of stretch in the material.

32. The apparatus according to claim 30 wherein said analyzing and comparing means includes a computer.

33. The apparatus according to claim 28 wherein said light intensity measurement means comprises a charged-coupled-device.

34. The apparatus according to claim 28 wherein said light intensity measurement means comprises an opto-electrical transducer.

35. The apparatus according to claim 28 wherein said light intensity measurement means includes means for measuring small chances in reflectance.

36. The apparatus according to claim 28 wherein said light intensity measurement means includes means for reducing optical noise; such that small changes in reflectance may be measured.

37. The apparatus according to claim 28 wherein said light intensity measurement means comprises a light sensitive photodiode.

38. The apparatus according to claim 28 wherein said two perpendicular orientations comprise a first direction associated with a field which is perpendicular to the plane of incidence and a second direction associated with a field which is parallel to the plane of incidence.

39. The apparatus according to claim 28 wherein said light source comprises a laser.

40. The apparatus according to claim 39 wherein said laser is an argon laser.

41. The apparatus according to claim 28 further comprising fiber optic cable for delivering the light beam to the diffuse reflectance surface.

42. The apparatus according to claim 28 further comprising a means for mechanically chopping the light beam emanating from said light source.

43. The apparatus according to claim 28 wherein the light beam is targeted upon the surface of the object at a desired angle of incidence.

44. The apparatus according to claim 43 wherein said desired angle of incidence is in the approximate range of between 20 degrees and 80 degrees.

45. The apparatus according to claim 28 wherein said light analyzer means is positioned to collect the reflected light at an angle which is substantially equal to said angle of incidence.

46. The apparatus according to claim 28 wherein said light analyzer means comprises an adjustable iris for aperturing the collected reflected light beam, and a lens for focusing the collected reflected light beam onto said light intensity measurement means.

47. The apparatus according to claim 28 further comprising a lock-in amplifier for measuring the light intensity incident on the reflection measurement means.

48. The apparatus according to claim 28 wherein said laser emits light having a wavelength less than 600 nm.

49. The apparatus according to claim 28 including a noise suppression circuit adapted to reduce the effect of noise upon sensitive measurements.

50. The apparatus according to claim 49 wherein said noise suppression circuit includes a mechanical chopper.

51. The apparatus according to claim 49 wherein said noise suppression circuit includes a mechanical chopper and lock-in amplifier.

52. The apparatus according to claim 51 wherein said light intensity measurement means cooperates with said noise suppression circuit to form each of said light intensity measurements from a plurality discrete samples of light.

53. The apparatus of claim 28 wherein said light intensity measurements represent diffuse reflectance.

54. The apparatus of claim 52 wherein said light intensity measurements represent diffuse reflectance.

55. A method for quantitatively assessing the amount of stress by measuring stretch induced by an applied load on an object which has a diffuse reflectance surface, the method comprising the following sequence of steps:

producing a light beam;

polarizing the light beam into a desired first of two perpendicular orientations which include a first orientation wherein the incident light is polarized perpendicular to the plane of incidence (s polarization) and a second orientation wherein the incident light is polarized parallel to the plane of incidence (p polarization);

exposing the diffuse reflectance surface of the object to the incident chopped, polarized light beam;

polarizing at least a portion of the light reflected from the diffuse reflectance surface into the desired first of said two perpendicular orientations; and detecting the intensity of the polarized, reflected light of the first orientation;

wherein the amount of stretch induced by the applied load on the object is correlated to the intensity of polarized, reflected light and determining the amount of stress by measuring stretch.

56. The method according to claim 55 further comprising the following sequence of steps:

polarizing the light beam into a desired second of said two perpendicular orientations;

exposing the diffuse reflectance surface of the object to the incident chopped, polarized light beam of the desired second orientation;

polarizing at least a portion of the light reflected from the diffuse reflectance surface into the desired second orientation;

detecting the intensity of the polarized, reflected light of the second orientation; and obtaining the difference between the intensities of the polarized, reflected light at the first and second orientations;

wherein the amount of stretch induced by the applied load on the object is correlated to the difference in the intensities of the polarized, reflected light at the two orientations.

57. The method according to claim 55 further comprising focusing the incident light beam.

58. The method according to claim 55 further comprising collecting the reflected light at an angle which is substantially equal to the angle of incident light.

59. The method according to claim 55 further comprising aperturing at least a portion of the reflected light in order to define a solid angle of collected light prior to measuring changes in the reflection characteristics.

60. The method according to claim 55 further comprising focusing at least a portion of the reflected light prior to measuring changes in the reflection characteristics.

61. The method according to claim 55 further including the step of suppressing noise in light detected by said detecting step.

62. The method according to claim 61 wherein said suppressing noise step includes limiting the intensity of the incident light beam.

63. The method according to claim 62 wherein said suppressing noise step includes mechanically chopping the incident light beam.

64. The method according to claim 63 further comprising providing a lock-in amplifier with phase sensitive detection in synch with the mechanical chopping, wherein said lock-in amplifier produces a signal which is indicative of the intensity of the light reflected from the diffuse reflectance surface measured from a plurality of discrete samples.

65. The method according to claim 55 wherein said object is elastic or viscoelastic.

66. The method according to claim 55 wherein said object is biological or non-biological.

* * * * *